US006599528B1

(12) United States Patent
Rosenberg et al.

(10) Patent No.: US 6,599,528 B1
(45) Date of Patent: Jul. 29, 2003

(54) MECHANICALLY STABLE PHARMACEUTICAL PRESENTATIONS FORM CONTAINING LIQUID OR SEMISOLID SURFACE-ACTIVE SUBSTANCES

(75) Inventors: Jörg Rosenberg, Ellerstadt (DE); Gunther Berndl, Herxheim (DE); Bernd Liepold, Mannheim (DE); Jörg Breitenbach, Mannheim (DE)

(73) Assignee: Abbott GmbH & Co. KG, Ludwigshafen (DE)

( * ) Notice: Subject to any disclaimer, the term of this patent is extended or adjusted under 35 U.S.C. 154(b) by 0 days.

(21) Appl. No.: 09/936,349

(22) PCT Filed: Mar. 17, 2000

(86) PCT No.: PCT/EP00/02381

§ 371 (c)(1),
(2), (4) Date: Sep. 11, 2001

(87) PCT Pub. No.: WO00/57854

PCT Pub. Date: Oct. 5, 2000

(30) Foreign Application Priority Data

Mar. 25, 1999 (DE) ............................................ 199 13 692

(51) Int. Cl.⁷ .............................. A61K 9/48; A61K 9/20
(52) U.S. Cl. ....................................... 424/451; 424/464
(58) Field of Search .................................. 424/451, 464

(56) References Cited

U.S. PATENT DOCUMENTS

| 4,801,460 A | 1/1989 | Goertz et al. ................ 424/465 |
| 4,880,585 A | 11/1989 | Klimesch et al. ............ 264/141 |
| 4,904,699 A | 2/1990 | Bauer .......................... 514/972 |
| 5,695,784 A | 12/1997 | Pollinger et al. ............ 424/495 |
| 5,707,648 A | * 1/1998 | Yiv ............................. 424/450 |
| 5,834,472 A | 11/1998 | Sangekar et al. ............ 514/252 |

FOREIGN PATENT DOCUMENTS

| EP | 240 904 | 10/1987 |
| EP | 240 906 | 10/1987 |
| EP | 272 336 | 6/1988 |
| EP | 551 820 | 7/1993 |

OTHER PUBLICATIONS

Voigt "Pharmazeutische Technologie" (1993) pp. 80–85.

* cited by examiner

*Primary Examiner*—Carlos Azpuru
(74) *Attorney, Agent, or Firm*—Keil & Weinkauf

(57) ABSTRACT

The present invention relates to mechanically stable pharmaceutical presentations for oral administration, comprising in addition to one or more active ingredients and at least one melt-processable matrix-forming excipient more than 10 and up to 40% by weight of a surface-active substance with an HLB of from 2 to 18, which is liquid at 20° C. or has a drop point in the range from 20 to 50° C.

6 Claims, No Drawings

MECHANICALLY STABLE PHARMACEUTICAL PRESENTATIONS FORM CONTAINING LIQUID OR SEMISOLID SURFACE-ACTIVE SUBSTANCES

BACKGROUND OF THE INVENTION

The present invention relates to mechanically stable pharmaceutical presentations for oral administration, comprising in addition to one or more active ingredients and at least one melt-processable matrix-forming excipient more than 10 and up to 40% by weight of a surface-active substance with an HLB of from 2 to 18, which is liquid at 20° C. or has a drop point in the range from 20 to 50° C. A process for producing such forms has also been found.

The production of pharmaceutical preparations by the melt extrusion process is known per se. Thus, the process described, for example, in EP-A 240 904 or EP-A 240 906 makes it possible, by a specific selection and defined mixtures of the excipients employed, to control specifically the properties of the formulations to be produced.

For example, it is possible to produce, by selecting suitable matrix polymers, preparations which release the active ingredient continuously over a lengthy period. On the other hand, it may be desirable, for example in the case of analgesics, for the active ingredient to dissolve rapidly and be released quickly. The melt extrusion process has proven to be suitable for producing rapid release and slow release formulations.

A basic requirement is, however, that the active ingredient is able to dissolve sufficiently in the aqueous medium in the digestive tract. Absorption of the active ingredient is possible only if it is in dissolved form, because only dissolved active ingredients can cross the intestinal wall. Active ingredients of low solubility may therefore not be absorbed sufficiently and, associated with this, have a low bioavailability.

There have been no lack of attempts to improve the bioavailability of active ingredients of low solubility (cf. R. Voigt; "Pharmazeutische Technologie", published by Ullstein Mosby, 7th edition, 1993, pages 80–85). In particular, the production of coevaporates or so-called solid dispersions, in which the active ingredient is in the form of a molecular dispersion in an excipient matrix, has frequently proved advantageous for increasing the bioavailability. When the drug form dissolves in the body, the active ingredient can be released in molecular form from such solid dispersions directly and without supplying energy of salvation.

However, the use of solid dispersions has a beneficial effect on the bioavailability of the active ingredient only if the active ingredient can also undergo rapid absorption. However, if the absorption process is slow, the active ingredient of low solubility recrystallizes in the aqueous medium of the intestinal lumen because a supersaturated solution of active ingredient may be produced on dissolution of the drug form. For this reason, the bioavailabilities which can be achieved even with solid dispersions are often unsatisfactory.

The absorption of the active ingredient is often insufficient also because the active ingredient is released too slowly from the tablet. Absorption of most active ingredients into the blood circulation takes place in the upper sections of the small intestine, i.e. relatively soon after passing through the stomach. Active ingredients which have not been adequately solubilized on reaching this region of the small intestine can be absorbed to only a limited extent.

It is therefore crucial for achieving optimal absorption rates, especially of active ingredients of low solubility which readily crystallize, to achieve rapid and sufficiently long-lasting solubilization in the aqueous medium of the digestive tract without recrystallization occurring.

The addition of surface-active substances is appropriate for this. The addition of surface-active substances to formulations of active ingredients of low solubility is generally known per se.

U.S. Pat. No. 5,834,472 discloses, for example, that the bioavailability of an antifungal agent can be improved by using a nonionic surface-active substance.

However, since most surface-active substances are liquid or semisolid at room temperature, the preparations produced to date are usually oily liquids or semisolids used to fill hard or soft gelatin capsules. However, in the case of soft gelatin capsules, interactions between excipients and the gelatin shell of the capsule are frequent and lead to leakage from the capsule.

The use of surface-active substances in tablet formulations is not possible without problems either because the liquid or semisolid surface-active substances impede compressibility in the conventional tableting process, especially when larger amounts of surface-active substances in the region of more than 10% by weight are needed to solubilize the active ingredient.

It is an object of the present invention to find mechanically stable solid formulations for oral use which can be used in particular for rapid and nevertheless long-lasting solubilization of active ingredients of low solubility after they have been liberated from the drug form.

BRIEF SUMMARY OF THE INVENTION

We have found that this object is achieved by the pharmaceutical formulations defined at the outset, and a process for producing them.

DETAILED DESCRIPTION OF THE INVENTION

The active ingredients which can be used are in principle all human and veterinary pharmaceutical substances, and active ingredients used in food supplements.

Particularly suitable active ingredients are immunosuppressants, protease inhibitors, reverse transcriptase inhibitors, cytostatics or antimycotics, in addition to CNS-active substances or dihydropyrimidine derivatives.

It is possible in particular to formulate active ingredients of low solubility or low bioavailability according to the invention. Low solubility means that the solubility in an aqueous medium is less than 1 mg/ml. Such active ingredients are also referred to in USP XXII, page 8, as scarcely soluble or practically insoluble.

Examples of active ingredients of low solubility are esuprone, nifedipine, ciclosporin or Taxol.

Suitable and preferred surface-active substances are low molecular weight substances which have an HLB (HLB—hydrophilic lipophilic balance) and are liquid at 20° C. or have a drop point in the range from 20° C. to 50° C., preferably up to 40° C. Preferred substances have an HLB of from 7 to 18, particularly preferably 10 to 15.

Examples of suitable surface-active substances are saturated and unsaturated polyglycolized glycerides, semisynthetic glycerides, fatty acid esters or ethers of fatty alcohols as long as they have the properties stated above.

The corresponding sorbitan fatty acid esters or ethoxylated sorbitan fatty acid esters are particularly suitable, such as, for example, polyoxyethylene 20 sorbitan monolaurate, polyoxyethylene 20 sorbitan monopalmitate, polyoxyethylene 20 sorbitan monostearate, polyoxyethylene 20 sorbitan monooleate, polyoxyethylene 20 sorbitan tristearate, polyoxyethylene 20 sorbitan trioleate, polyoxyethylene 4 sorbitan monostearate, polyoxyethylene 4 sorbitan monolaurate or polyoxyethylene 4 sorbitan monooleate. Also suitable are macrogol 6 cetylstearyl ether or macrogol 25 cetylstearyl ether.

Particular preference is given to polyoxyethylene glycerol ricinoleate 35, polyoxyethylene glycerol trihydroxystearate 40, PEG 660 12-hydroxystearate (polyglycol ester of 12-hydroxystearic acid (70 mol%) with 30 mol% ethylene glycol).

The surface-active substances are present in the preparations in amounts of more than 10% by weight based on the total weight of the preparation, and up to 40% by weight, preferably 15 to 25% by weight and particularly preferably 20 to 25% by weight.

The preparations according to the invention also comprise at least one melt-processable matrix excipient. Particularly suitable matrix-forming excipients are water-soluble pharmaceutically acceptable polymers or sugar alcohols or mixtures thereof as long as they can be melted without decomposition.

Pharmaceutically acceptable polymers are, in particular, homo- and copolymers of N-vinylpyrrolidone such as polyvinylpyrrolidone with Fikentscher K values of from 12 to 100, in particular K 17 to K 30, or copolymers with vinyl carboxylates such as vinyl acetate or vinyl propionate, for example copovidone (VP/VAc-60/40).

Also suitable are polyvinyl alcohol or polyvinyl acetate, which may also be partially hydrolyzed, or acrylate polymers of the Eudragit type.

Also suitable are cellulose derivatives such as hydroxyalkylcelluloses, for example hydroxypropylcellulose, or, if slower release is required, hydroxyalkylalkylcelluloses which swell in water, for example hydroxypropylmethylcellulose (HPMC), preferably with degrees of methoxy substitution in the region of 22% and degrees of hydroxypropoxy substitution in the region of 8%, particularly preferably HPMC types with viscosities of 4000 mPas, 15,000 mPas or 100,000 mPas, measured at 20° C. in 2% by weight aqueous solution. Also suitable are HPMC types with degrees of methoxy substitution in the range from 28 to 29% and degrees of hydroxypropoxy substitution in the range from 5 to 8.5%.

Likewise suitable are meltable sugar alcohols such as, for example, sorbitol, maltitol, isomalt, mannitol, xylitol, erythritol or mixtures thereof. Maltitol, mannitol, xylitol or isomalt is preferred.

Suitable matrix-forming polymers are also polyethylene glycols with molecular weights in the range from 1000 to 20,000,000 Dalton, preferably 4000 to 10,000 Dalton.

The preparations may additionally contain conventional pharmaceutical excipients such as flavorings, antioxidants, silicas, release agents or dyes in the amounts usual therefor.

The preparations according to the invention are produced by a melt process. The process is preferably carried out without addition of solvents.

The melt process is carried out in a kneader or a screw extruder. Examples of suitable kneaders are those supplied by Haake or Farrell.

The melt is preferably produced in a screw extruder, particularly preferably a twin screw extruder with and without kneading disks or similar mixing elements. Corotating twin screw extruders are particularly preferred.

Depending on the composition, the processing generally takes place at temperatures from 40° C. to 260° C., preferably 50 to 200° C.

The starting materials can be fed into the extruder or kneader singly or as premix. They are preferably added in the form of powdered or granulated premixes. Thus, the liquid or oily surface-active substance can previously be mixed with another starting material to give free-flowing granules. Addition of the surface-active substance in liquid form, for example by liquid pumps, which are preferably heated in the case of semisolid substances, is likewise possible.

It is also possible first to dissolve the active substance in the surface-active substance, and then to granulate this mixture with the polymer. In this case, the active ingredient must not itself melt.

It may also be advisable for temperature-sensitive active ingredients first to melt the other starting materials and only then to add the active ingredient.

The starting materials are accordingly processed together to form a melt, which is processed by input of mechanical energy, in particular in the form of shear forces, to a homogeneous composition.

The homogenous melt is then extruded through a die or a breaker plate and subjected to shaping. This can take place by pelletizing the extrudate by usual techniques, for example using rotating knives or compressed air, to result in pellets or granules. The shaping can also take place as described in EP-A 240 906, by the extrudate being passed between two counter-rotating calender rolls and being shaped directly to tablets. It is likewise possible to pass the melt through the open extruder head and, after solidification, further process where appropriate by grinding or by suitable granulation equipment such as roll mills or compacting units.

Granules or pellets can then be processed to tablets in conventional tablet presses. It is also possible for the preparations which have been initially obtained by calendering already in the form of mechanically stable tablets to be subjected to a grinding process and then to be compressed to tablets in a conventional way. If required, the tablets can then be provided with a conventional coating.

It is surprisingly possible according to the invention to obtain tablets which, despite a high proportion of liquid or semisolid surface-active substances, have good mechanical stability and are not prone to be tacky or to soften. The good dimensional stability of the preparations makes it unnecessary, according to the invention, to use them for filling capsules.

The resulting drug forms comprise the active ingredient embedded amorphously. The preferred result is solid dispersions in which the active ingredient is in the form of a molecular dispersion. The drug forms according to the invention make it possible for even active ingredients of low solubility to be sufficiently solubilized and stably dispersed in aqueous medium.

The preparations according to the invention form, after dissolving in aqueous medium, in particular at pH 1, for at least one hour a stable solubilizate or a stable dispersion, in which the active ingredient is preferably not in crystalline form.

EXAMPLE 1

50 g of a powdered mixture of 40% by weight of esuprone, 35% by weight of polyvinylpyrrolidone K 17

(PVP) and 25% by weight of polyoxyethylene glycerol trihydroxystearate 40 as surface-active substance were produced by initially producing a powdered premix of esupron and the PVP, into which the surface-active substance was mixed at 20° C. until homogeneous granules resulted.

EXAMPLE 2

The granules obtained in Example 1 were kneaded at a temperature of 100° C. in a heatable kneader (supplied by Haake) to a homogeneous melt. After cooling to 20° C., the melt was solid and was broken into small fragments.

EXAMPLE 3

250 g of the granules obtained in Example 1 were stirred into 50 ml of water at room temperature. There was formation after a few minutes of a cloudy suspension from which crystalline esuprone sedimented.

EXAMPLE 4

The melt granules obtained in Example 2 were stirred into water in analogy to Example 3. After only a few minutes an opalescent solution formed, and no esuprone had separated out of this even after one hour.

We claim:

1. A mechanically stable pharmaceutical presentation for oral administration, comprising one or more active ingredients, at least one melt-processable matrix-forming excipient selected from the group consisting of homo- and copolymers of N-vinylpyrrolidone, acrylate polymers and cellulose derivatives, and more than 10 and up to 40% by weight of a surface-active substance with an HLB of from 2 to 18, which is liquid at 20° C. or has a drop point in the range from 20 to 50° C., obtainable by mixing the starting materials in the melt without addition of solvents and subsequently shaping.

2. A preparation as claimed in claim 1, comprising from 15 to 25% by weight of surface-active substance.

3. A preparation as claimed in claim 1, comprising a surface-active substance with an HLB of from 10 to 15.

4. A preparation as claimed in claim 1, comprising a surface-active substance with a drop point in the range from 20 to 40° C.

5. A preparation as claimed in claim 1, comprising macrogol glycerol hydroxystearate, polyoxyethylene ricinoleate 35 or PEG 660 12-hydroxystearate as surface-active substance.

6. A process for producing mechanically stable pharmaceutical presentations as claimed in claim 1 by a melt process, which comprises processing one or more active ingredients, at least one melt-processable matrix-forming excipient and more than 10 and up to 40% by weight of a surface-active substance with an HLB of from 2 to 18, which is liquid at 20° C. or has a drop point in the range from 20 to 50° C., in the melt to a homogeneous mixture, and shaping the latter to presentations.

* * * * *